(12) United States Patent
Boser et al.

(10) Patent No.: US 9,402,989 B2
(45) Date of Patent: Aug. 2, 2016

(54) MEDICAL ELECTRICAL LEAD

(75) Inventors: Gregory A. Boser, Richfield, MN (US); Kevin R. Seifert, Forest Lake, MN (US); Greg Garlough, Bloomington, MN (US)

(73) Assignee: Medtronic, Inc., Minneapolis, MN (US)

( * ) Notice: Subject to any disclaimer, the term of this patent is extended or adjusted under 35 U.S.C. 154(b) by 2042 days.

(21) Appl. No.: 12/211,070

(22) Filed: Sep. 15, 2008

(65) Prior Publication Data

US 2009/0076578 A1     Mar. 19, 2009

Related U.S. Application Data

(60) Provisional application No. 60/972,114, filed on Sep. 13, 2007, provisional application No. 60/973,479, filed on Sep. 19, 2007.

(51) Int. Cl.
*A61N 1/05* (2006.01)

(52) U.S. Cl.
CPC ................. *A61N 1/05* (2013.01); *A61N 1/0563* (2013.01); *Y10T 29/49123* (2015.01); *Y10T 29/49204* (2015.01)

(58) Field of Classification Search
USPC .................................................. 607/115–116
See application file for complete search history.

(56) References Cited

U.S. PATENT DOCUMENTS

| | | | |
|---|---|---|---|
| 4,947,866 A * | 8/1990 | Lessar et al. | 607/116 |
| 5,358,516 A * | 10/1994 | Myers et al. | 607/116 |
| 5,393,929 A | 2/1995 | Yagihashi | |
| 5,609,622 A | 3/1997 | Soukup et al. | |
| 5,935,159 A | 8/1999 | Cross, Jr. et al. | |
| 7,519,432 B2 | 4/2009 | Bolea et al. | |
| 2004/0167595 A1 | 8/2004 | Tuominen | |
| 2005/0103518 A1 | 5/2005 | Glew | |
| 2005/0137671 A1 | 6/2005 | Liu et al. | |
| 2006/0089691 A1 | 4/2006 | Kaplan et al. | |
| 2006/0265037 A1 * | 11/2006 | Kuzma | 607/116 |
| 2006/0282144 A1 | 12/2006 | Knapp et al. | |
| 2007/0250143 A1 * | 10/2007 | Sommer | 607/116 |
| 2008/0234792 A1 | 9/2008 | Reddy et al. | |

FOREIGN PATENT DOCUMENTS

| | | |
|---|---|---|
| JP | 410149728 A | 6/1998 |
| WO | WO 98/29055 | 7/1998 |
| WO | wo 01/91851 | 12/2001 |

OTHER PUBLICATIONS

U.S. Appl. No. 12/211,093, filed Sep. 15, 2008, entitled "Medical Electrical Lead".
U.S. Appl. No. 12/211,075, filed Sep. 15, 2008, entitled "Medical Electrical Lead".
U.S. Appl. No. 12/211,065, filed Sep. 15, 2008, entitled "Medical Electrical Lead".

(Continued)

*Primary Examiner* — Carl H Layno
*Assistant Examiner* — Jon Eric C Morales
(74) *Attorney, Agent, or Firm* — Carol F. Barry

(57) ABSTRACT

A medical device lead. The lead includes one or more jacketed conductive elements. The jacket comprises one or more covers. A first cover of polytetrafluoroethylene (PTFE) is in direct contact with the at least one conductive element. The at least one conductive element and the PTFE cover are coiled. The coiled conductive element can substantially retain its original coiled shape.

6 Claims, 12 Drawing Sheets

(56) References Cited

OTHER PUBLICATIONS

U.S. Appl. No. 12/211,092, filed Sep. 15, 2008, entitled "Medical Electrical Lead".
U.S. Appl. No. 12/211,096, filed Sep. 15, 2008, entitled "Medical Electrical Lead".
PCT Search Report, PCT/US2008/010781, 3 pages.
International Search Report and Written Opinion of international application No. PCT/US2008/010788, mailed Feb. 18, 2009, 11 pp.
International Search Report and Written Opinion of international application No. PCT/US2008/010787, mailed Mar. 3, 2009, 11 pp.
International Search Report and Written Opinion of international application No. PCT/US2008/010786, mailed Mar. 3, 2009, 11 pp.
International Search Report and Written Opinion of international application No. PCT/US2008/010789, mailed Jul. 20, 2009, 15 pp.
International Search Report and Written Opinion of international application No. PCT/US2008/010781, mailed Feb. 18, 2009, 11 pp.
International Search Report and Written Opinion of international application No. PCT/US2008/010785. mailed Feb. 18, 2009, 11 pp.
Office Action from U.S. Appl. No. 12/211,096 dated Jun. 8, 2010, 12 pp.
International Preliminary Report on Patentability from PCT Application No. PCT/US2008/010788, issue date Mar. 16, 2010, 7 pp.
International Preliminary Report on Patentability from PCT Application No. PCT/US2008/010789, issue date Mar. 16, 2010, 9 pp.

* cited by examiner

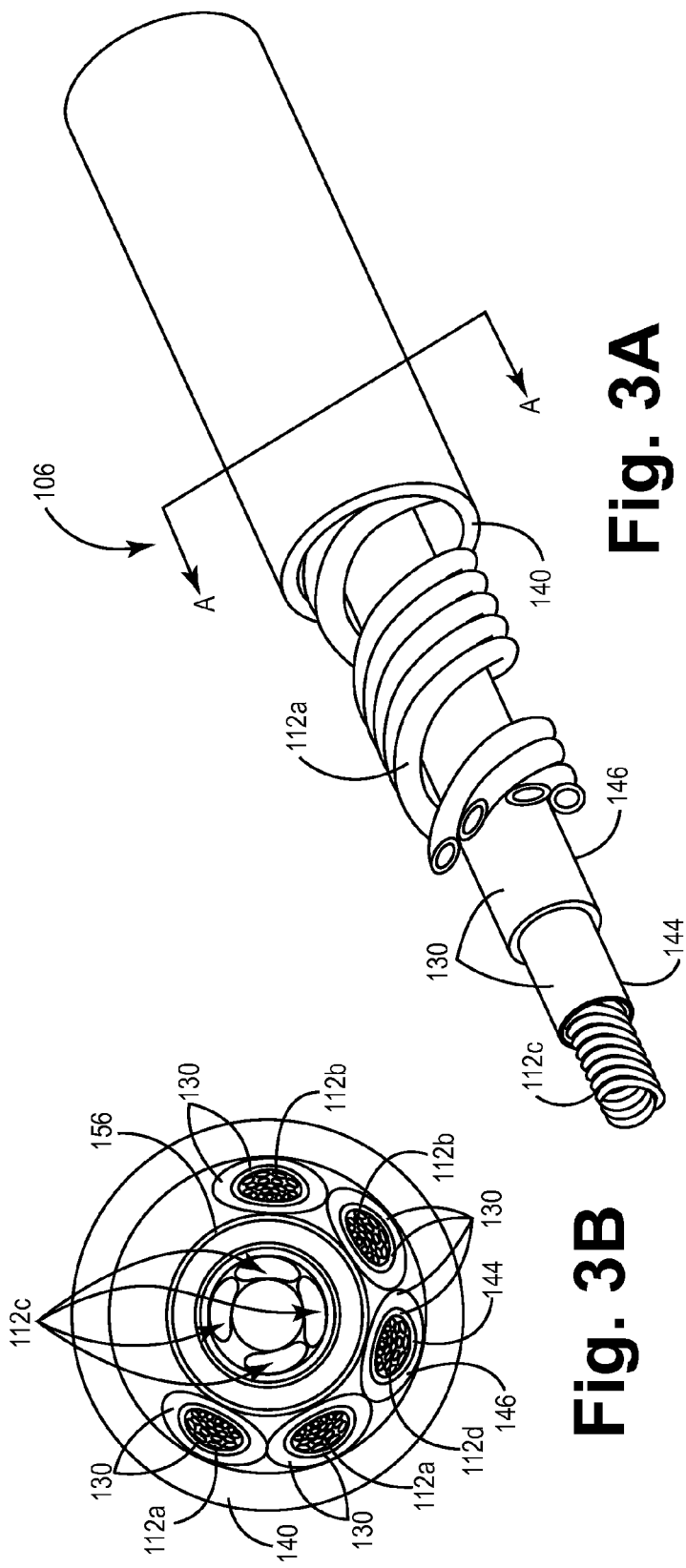

MEDICAL ELECTRICAL LEAD

CROSS-REFERENCE TO RELATED APPLICATION

The present application claims priority and other benefits from U.S. Provisional Patent Application Ser. No. 60/973,479 filed Sep. 19, 2007, incorporated herein by reference in its entirety. The present application also claims priority and other benefits from U.S. Provisional Patent Application Ser. No. 60/972,114 filed Sep. 13, 2007, incorporated herein by reference in its entirety.

TECHNICAL FIELD

The disclosure relates to implantable medical devices and, more particularly, to implantable medical leads.

BACKGROUND

The human anatomy includes many types of tissues that can either voluntarily or involuntarily, perform certain functions. After disease, injury, or natural defects, certain tissues may no longer operate within general anatomical norms. For example, after disease, injury, time, or combinations thereof, the heart muscle may begin to experience certain failures or deficiencies. Certain failures or deficiencies can be corrected or treated with implantable medical devices (IMDs), such as implantable pacemakers, implantable cardioverter defibrillator (ICD) devices, cardiac resynchronization therapy defibrillator devices, or combinations thereof.

IMDs detect and deliver therapy for a variety of medical conditions in patients. IMDs include implantable pulse generators (IPGs) or implantable cardioverter-defibrillators (ICDs) that deliver electrical stimuli to tissue of a patient. ICDs typically comprise, inter alia, a control module, a capacitor, and a battery that are housed in a hermetically sealed container with a lead extending therefrom. It is generally known that the hermetically sealed container can be implanted in a selected portion of the anatomical structure, such as in a chest or abdominal wall, and the lead can be inserted through various venous portions so that the tip portion can be positioned at the selected position near or in the muscle group. When therapy is required by a patient, the control module signals the battery to charge the capacitor, which in turn discharges electrical stimuli to tissue of a patient through via electrodes disposed on the lead, e.g., typically near the distal end of the lead. Typically, a medical electrical lead includes a flexible elongated body with one or more insulated elongated conductors. Each conductor electrically couples a sensing and/or a stimulation electrode of the lead to the control module through a connector module. It is desirable to develop implantable medical electrical leads with new lead body subassemblies.

BRIEF DESCRIPTION OF DRAWINGS

Aspects and features of the present invention will be appreciated as the same becomes better understood by reference to the following detailed description of the embodiments of the invention when considered in connection with the accompanying drawings, wherein:

FIG. 3A is a schematic view of a distal end of the medical electrical lead;

FIG. 3B is a cross-sectional view taken along plane A-A of the distal end of the medical electrical lead depicted in FIG. 3A;

DETAILED DESCRIPTION

Figure 1:
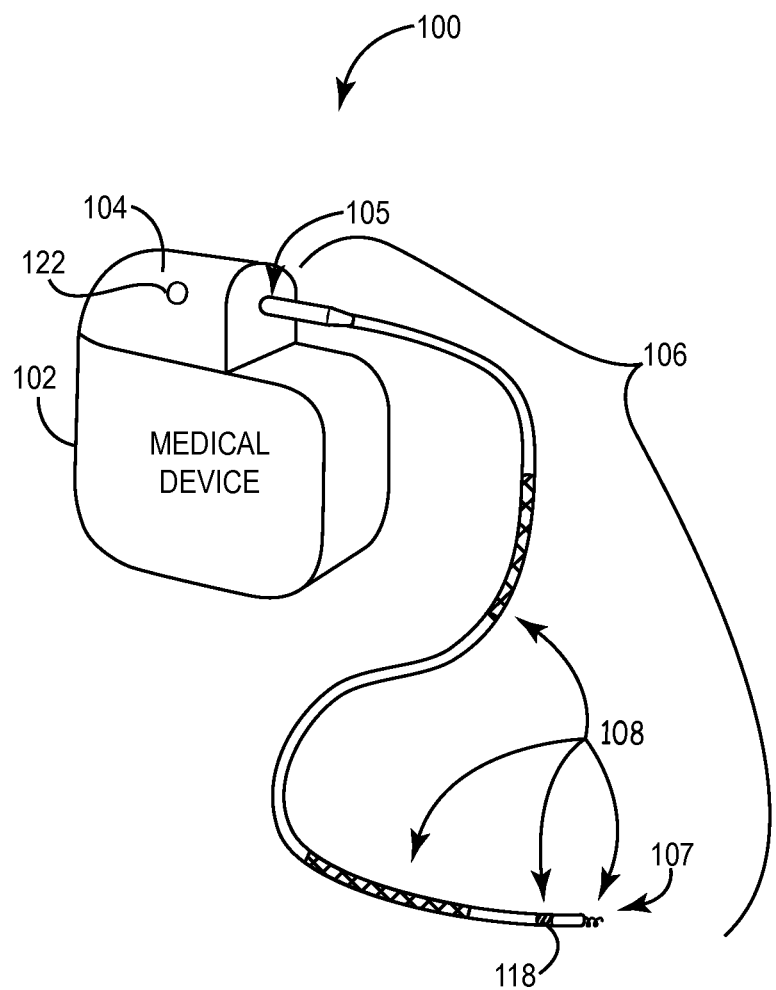
FIG. 1 is a conceptual schematic view of an implantable medical device in which a medical electrical lead extends therefrom.

The present disclosure relates to a medical electrical lead that includes a lead body. The lead body comprises at least one elongated conductive element, such as a cable, surrounded by an elongated jacket. The jacket can include one or more covers. The jacket can be formed through an extrusion process directly over the conductive element, which reduces or eliminates diametrical expansion of the coiled conductive element which can occur due to elastic "springback" or stress relaxation of the coiled composite structure. A first cover comprises ethylene-tetraflouroethylene (ETFE) extruded directly over the conductive element. In one embodiment, the conductive element and the jacket, is then formed into a coil.

In one embodiment, the PEEK undergoes a molecular mobility process prior to or during introduction of the ETFE over an elongated conductive element. Exemplary molecular mobility processes can include thermal annealing, stress relieving, or other suitable means for a material to achieve a more flexible molecular structure.

Thermal processing can involve exposing the composite structure to a controlled heating and cooling schedule. Suitable temperatures can depend upon the type of polymeric material and/or number of covers or layer(s) employed, to form a jacket, a composite jacket, or one or more longitudinal elements that can house conductive elements. ETFE, for example, can be thermally processed at about 130-200 degrees Celsius (° C.). Thermal processing of ETFE onto an elongated conductive element causes the conductive element to substantially maintain a controlled pitch and diameter after coiling. For example, a conductive element such as a cable in a coil shape can substantially maintain up to about 99 percent of its original coil shape, after the conductive element has been released from, for example, a mandrel which is after a thermal processing has been performed. The final diameter and pitch of a coil shape is generally based upon the coil composite structure and its elastic "springback" or coil expansion from stress relaxation, the winding diameter/pitch, and the processing parameters used to set the coil shape. In one embodiment, a coiled cable is more resistant to flex fatigue compared to a linear or straight cable. Additionally, smaller coiled cable diameters are achieved through application of the principles described herein. In one embodiment, about 10 percent or more of a diameter reduction in the coiled conductive element is achieved through the principles described herein. In another embodiment, about 5 percent or more diameter reduction is achieved in the coiled conductive element through the principles described herein. In still yet another embodiment, about 2 percent or more diameter reduction is achieved in the coiled conductive element through the principles described herein. Smaller coiled cable diameters allow for smaller sized leads to be produced. Smaller sized leads can include 7 French or smaller. In another embodiment, smaller sized leads can include 6 French or smaller. In still yet another embodiment, smaller sized leads can include 5 French or smaller.

The principles described herein are applicable to all types of medical electrical leads. For example, the disclosure applies to cardiovascular leads (e.g. high voltage leads, low voltage leads etc.), neurological leads, or other suitable applications.

FIG. 1 depicts a medical device system 100. A medical device system 100 includes a medical device housing 102 having a connector module 104 (e.g. international standard (IS)-1, defibrillation (DF)-1, IS-4 etc.) that electrically couples various internal electrical components housed in medical device housing 102 to a proximal end 105 of a medical electrical lead 106. A medical device system 100 may comprise any of a wide variety of medical devices that include one or more medical lead(s) 106 and circuitry coupled to the medical electrical lead(s) 106. An exemplary medical device system 100 can take the form of an implantable cardiac pacemaker, an implantable cardioverter, an implantable defibrillator, an implantable cardiac pacemaker-cardioverter-defibrillator (PCD), a neurostimulator, a tissue and/or muscle stimulator. IMDs are implanted in a patient in an appropriate location. Exemplary IMDs are commercially available as including one generally known to those skilled in the art, such as the Medtronic CONCERTO™, SENSIA™, VIRTUOSO™, RESTORE™, RESTORE ULTRA™, sold by Medtronic, Inc. of Minnesota. Non-implantable medical devices or other types of devices may also utilize batteries such as external drug pumps, hearing aids and patient monitoring devices or other suitable devices. Medical device system 100 may deliver, for example, pacing, cardioversion or defibrillation pulses to a patient via electrodes 108 disposed on distal end 107 of one or more lead(s) 106. Specifically, lead 106 may position one or more electrodes 108 with respect to various cardiac locations so that medical device system 100 can deliver electrical stimuli to the appropriate locations.

Figure 2:
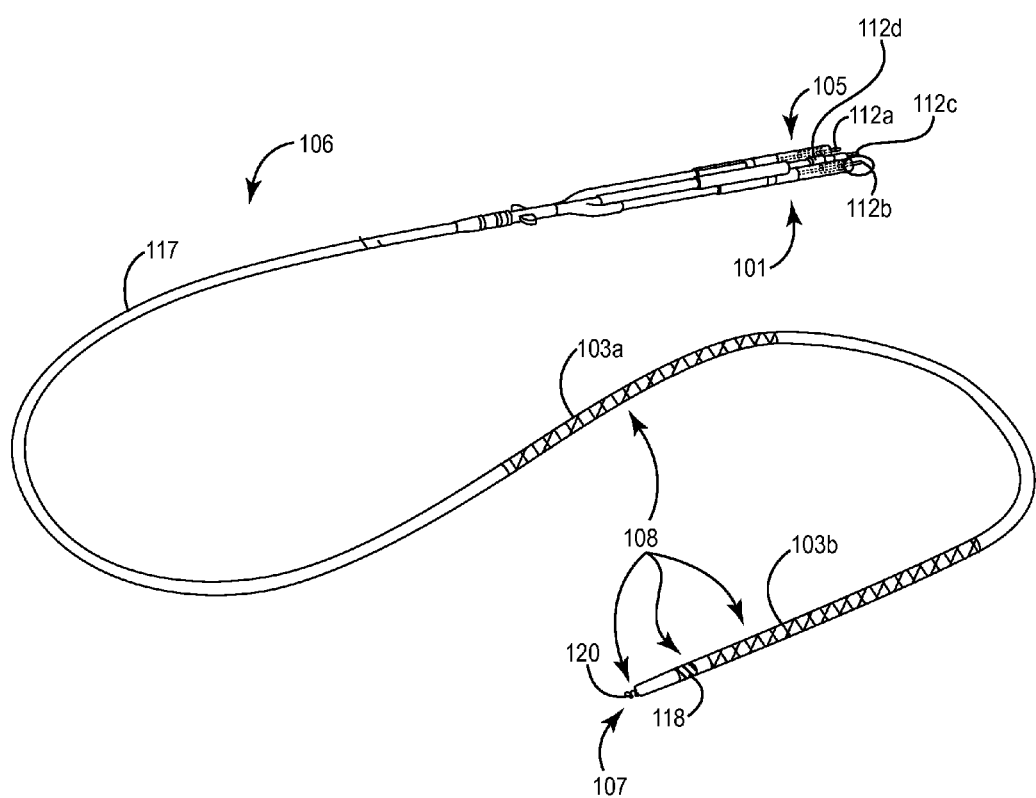
FIG. 2 is a schematic view of a medical electrical lead.

FIG. 2 depicts lead 106. Lead 106 includes a lead body 117 that extends from proximal end 105 to a distal end 107. Lead body 117 can include one or more connectors 101, and one or more jacketed conductive elements 112a-d. A jacket (also referred to as a liner, longitudinal element, coating) extends along and longitudinally around the conductive elements 112a-d and can serve to contain or mechanically constrain one or more conductive elements 112a-d. A jacket can also insulate one or more conductive elements 112a-d. Connector module 104 can contain connectors 122, such as set screws, serve to electrically and mechanically connect conductive elements 112a-d to ports (not shown) of connector module 104. Conductive element 112c (also referred to as a "conductor coil," "torque coil", "distal tip conductor") can extend to the distal end 107 and can optionally be coupled to a retractable and/or extendable helical tip. One or more conductive elements 112a,b serve as, or are connected to, defibrillation coils 103a,b that deliver electrical stimuli, when necessary, to tissue of a patient. Lead 106 can also include a conductive element 112d that extends from the proximal end 105 to ring electrode 118 while another conductive element 112c extends from proximal end 105 to tip electrode 120.

Electrically conductive elements 112a-d can include coils, wires, coil wound around a filament, cables, conductors or other suitable members. Conductive elements 112a-d can comprise platinum, platinum alloys, titanium, titanium alloys, tantalum, tantalum alloys, cobalt alloys (e.g. MP35N, a nickel-cobalt alloy etc.), copper alloys, silver alloys, gold, silver, stainless steel, magnesium-nickel alloys, palladium, palladium alloys or other suitable materials. Electrically conductive element 112a-d is covered, or substantially covered, longitudinally with a jacket 130 (also referred to as a liner, a longitudinal element, a longitudinal member, a coating, a tubular element, a tube or a cylindrical element). In yet another embodiment, each conductive element 112a-d is surrounded by a tubular element, which can possess a circular or a non-circular cross-section. An outercover or outerjacket in a lead body 117 can exhibit a non-circular cross-section.

Typically, the outer surface of electrodes 108 such as the ring electrode 118, the tip electrode 120, and the defibrillation coils 103a,b are exposed or not covered by a jacket 130 or liner so that electrodes 108 can sense and/or deliver electrical stimuli to tissue of a patient. A sharpened distal tip (not shown) of tip electrode 120 facilitates fixation of the distal end of helically shaped tip electrode 120 into tissue of a patient.

Referring to FIGS. 3A-3B, and 4A-4B, lead body 117 can include one or more jackets 130 and one or more conductive elements 112a,b,d. In one embodiment, lead body 117 comprises one or more jackets 130 disposed in another jacket 130. In still yet another embodiment, lead body 117 comprises one or more jackets 130 with an outer cover 140 that surrounds the one or more jackets 130.

Figure 4A:
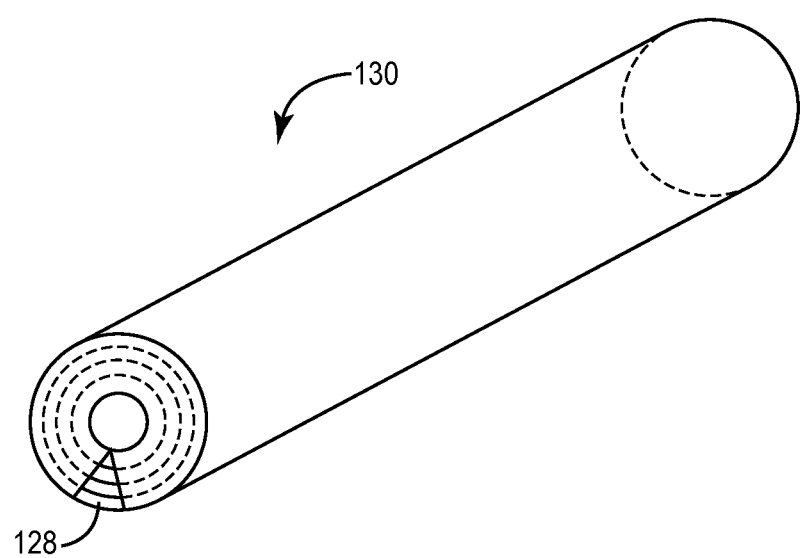
FIG. 4A is a schematic view of a jacket that surrounds one or more conductive elements in a medical electrical lead.
Figure 4B:
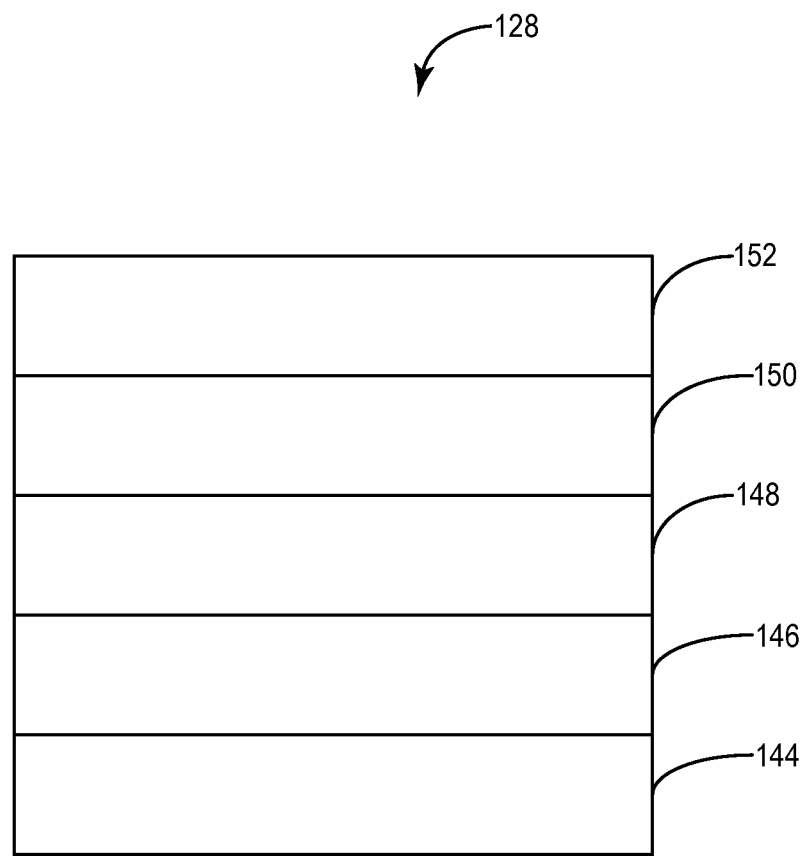
FIG. 4B is a schematic sectional view of the jacket depicted in FIG. 4A.

Each jacket 130 can include one or more covers, as depicted in FIGS. 4A-4B with cross-sectional segment 128. Each cover 146, 148, 150, and 152 can comprise one or more layers of polymeric compounds. Numerous embodiments of jacket 130 or liner are summarized in Table 1 and described in greater detail below. The first embodiment listed in Table 1 involves a single cover or first cover 144 of PEEK such that the inner lumen of first cover 144 is adjacent to a conductive element 112a,b,d, a delivery device (not shown) such as a guide wire or stylet, or a lumen without a delivery device, or a conductive element 112c such as a conductor coil. PEEK is commercially available as Optima from Invibio located in Lancashire, United Kingdom. The first cover 144 of PEEK can be formed in a variety of ways. In one embodiment, the single cover or first cover of PEEK may be introduced or applied directly over a conductive element 112a-d through extrusion. Extrusion is the process of forming a continuous shape by applying force to a material through a die. Polymer extrusion is described, for example, in Chris Rauwendaal, pp.

1-30, 155-205, *Polymer Extrusion* (4th ed. 2001), which is incorporated by reference in relevant part. Generally, the polymeric material is heated in a barrel of the extruder until it attains or exceeds its melt temperature. Thereafter, the polymeric material is simultaneously extruded through a die of the extruder over the conductive element 112a-d while the conductive element 112a-d continues to move away from the extruder and/or the conductive element 112a-d moves radially. The polymeric material then forms into a first cover 144 (also referred to as first longitudinal element) over the conductive element 112a-d. After formation of first cover 144, the polymeric material is allowed to cool. There are numerous ways to cool the polymeric material. For example, the first cover 144 can be air cooled, which is a slow cooling process. Alternatively, the first cover 144 can be placed in a cool water bath. In yet another embodiment, the first cover 144 and the conductive element 112a-d can be placed into a cooler such as a refrigeration unit to quickly cool the polymeric material. The process of extruding polymeric material and allowing the polymeric material applies to each embodiment listed below.

The cover of PEEK can have a thickness of about 0.0005 inches to about 0.0015 inches. In another embodiment, the cover of extruded PEEK can possess a thickness that ranges from about 0.00020 inches to about 0.0012 inches. In yet another embodiment, the cover of PEEK has a thickness of about 0.0005 inches to about 0.0020 inches. The PEEK in combination with the conductive element 112a-d forms a composite structure.

The composite structure is then formed into a coil shape. In one embodiment, the composite structure is formed into a coil through, for example, winding the conductive element 112a, b, d over a mandrel 702, a cylindrically shaped element, exemplarily depicted in FIG. 10A. In particular, the mandrel 702 can be a high tensile strength wire that is held under tension (i.e. both ends of the mandrel 702 are clamped) while the filars of the coil are wound around the diameter of the mandrel 702. While the mandrel 702 continues to rotate or move radially, filars of the coil are being wound or served around mandrel 702. The filars are simultaneously translated along mandrel 702 while being wound about mandrel 702. An exemplary amount of winding tension applied is about 15 grams; however, it is appreciated that other amounts of winding tensions can be used The amount of tension used can depend upon the geometry and/or the mechanical characteristics (e.g. break load or strength of the cable filars, yield strength of the cable filars, etc.) of the cable filars that are to be formed. Coil winding equipment is commercially available from Accuwinder Engineering Company located in San Dimas, Calif.

The coiled conductive element 112a,b,d can be mechanically constrained to minimize or eliminate diametrical and/or axial expansion of the coiled conductive element 112a,b,d. Exemplary methods for mechanically constraining the conductive element 112a,b,d can include clamping or bonding the proximal and distal ends of 112a,b,d to a mandrel 702 or other suitable fixture or component. The clamp(s) or clamp mechanism(s) can mechanically constrain or secure the coiled conductive element 112a,b,d against the mandrel 702, as depicted, for example, in FIG. 10 such that coiled conductive element 112a,b,d will not rotate or expand diametrically and/or axially. Exemplary clamping mechanisms can take the form of a mechanical clamp, toggle(s) or heat shrink tubing (s). The clamping mechanism can mechanically constrain the coil conductive element on the mandrel and hold the coiled conductive element in place during subsequent operations.

In one embodiment, after the extrusion coating process and the coiling process, no thermal processing is performed on the coiled conductive element 112a,b,d. In another embodiment, after the extrusion coating process and the coiling process, thermal processing is performed on the coiled conductive element 112a,b,d. In still yet another embodiment, after the extrusion coating process, thermal processing is performed on the conductive element 112a,b,d which is thereafter followed by a coiling process to coil the conductive element 112a,b,d. In yet another embodiment, after the extrusion coating process, the coiled conductive element 112a,b,d is thermal processed and can then undergo a coiling process. After coiling process, the coiled conductive element 112a,b,d undergoes a second thermal process.

The composite structure can then undergo a thermal process; however, it is appreciated that a thermal process may be unnecessary to form, for example, a coiled cable assembly. In one embodiment, the composite structure is placed or run through a chamber. For example, a chamber or oven, commercially available from Despatch Industries, Minneapolis, Minn., can be used to process the composite structure. In one embodiment, the temperature in the chamber is about 130° C. to about 210° C. In one embodiment, the temperature in the chamber is about 130° C. to about 210° C. The composite structure remains at this temperature for about 30 seconds to about 45 minutes and then is cooled to form the ETFE polymeric material and conductive element 112a,b,d in its coiled shape. The mechanical constraint is then removed such as through de-clamping or cutting the proximal and distal ends of the conductive element 112 from the mandrel.

The first embodiment listed in Table 1 relates to a jacket 130 formed of a first cover 144. First cover 144 of ethylenetetrafluoroethylene (ETFE) can possess a thickness that ranges from about 0.0005 inches to about 0.0015 inches of extruded ETFE. In another embodiment, first cover 144 can possess a thickness that ranges from about 0.00020 inches to about 0.003 inches. A composite structure is composed of the first cover 144 over the conductive element 112a,b,d. The composite structure is formed into a coil shape and then mechanically constrained, as previously described.

The composite structure then undergoes thermal annealing or stress relieving in a chamber. The temperature in the chamber is about 130° C. to about 210° C. for about 30 seconds to about 30 minutes to allow the polymeric material to form jacket 130 around conductive element 112a,b,d. Thereafter, the mechanical constraint is removed.

The second embodiment listed in Table 1 relates to a jacket 130 formed of a first, and second covers 144, 146. First cover 144 of ETFE can possess a thickness that ranges from about 0.0005 inches to about 0.0015 inches of extruded ETFE. In another embodiment, first cover 144 can possess a thickness that ranges from about 0.00020 inches to about 0.003 inches. In another embodiment, first cover 144 can possess a thickness that ranges from about 0.00020 inches to about 0.001 inches. First cover 144 of ETFE is formed by extruding the ETFE over a conductive element 112a,b,d. After the first cover 144 of ETFE has been formed, a second cover 146 of ETFE is introduced over the first cover 144. Second cover 146 can possess a thickness that ranges from about 0.00020 inches to about 0.001 inches. A composite structure is composed of the first, and second covers 144, 146 respectively, over the conductive element 112a,b,d. The composite structure is formed into a coil shape and then mechanically constrained, as previously described.

The composite structure then undergoes thermal annealing or stress relieving in a chamber. The temperature in the chamber is about 130° C. to about 210° C. for about 30 seconds to about 30 minutes to allow the polymeric material to form jacket 130 around conductive element 112a,b,d. Thereafter, the mechanical constraint is removed.

The third embodiment listed in Table 1 relates to a jacket 130 formed of a first, second and third covers 144, 146, 148. First cover 144 of ETFE can possess a thickness that ranges from about 0.0005 inches to about 0.0015 inches of extruded ETFE. In another embodiment, first cover 144 can possess a thickness that ranges from about 0.00020 inches to about 0.001 inches. First cover 144 of ETFE is formed by extruding the ETFE over a conductive element 112a,b,d. After the first cover 144 of ETFE has been formed, a second cover 146 of ETFE is introduced over the first cover 144. Second cover 146 can possess a thickness that ranges from about 0.00020 inches to about 0.001 inches. A third cover 148 of ETFE is introduced over the second cover 146 in which the third cover 148 can possess a thickness that ranges from about 0.00020 inches to about 0.001 inches. A composite structure is composed of the first, second, and third covers 144, 146, 148 respectively, over the conductive element 112a,b,d. The composite structure is formed into a coil shape and then mechanically constrained, as previously described.

The composite structure then undergoes thermal annealing or stress relieving in a chamber. The temperature in the chamber is about 130° C. to about 210° C. for about 30 seconds to about 30 minutes to allow the polymeric material to form jacket 130 around conductive element 112a,b,d. Thereafter, the mechanical constraint is removed.

The fourth embodiment listed in Table 1 involves a first cover 144 of ETFE followed by a second cover 146 of fluorinated ethylene propylene (FEP). First cover 144 of ETFE can possess a thickness that ranges from about 0.0005 inches to about 0.0015 inches of extruded ETFE. In another embodiment, first cover 144 can possess a thickness that ranges from about 0.00020 inches to about 0.001 inches. After the first cover 144 of ETFE has been formed, a second cover 146 of FEP is introduced over the first cover 144. Second cover 146 can possess a thickness that ranges from about 0.00020 inches to about 0.001 inches. In another embodiment, second cover 146 can possess a thickness that ranges from about 0.00020 inches to about 0.003 inches. The composite structure, comprised of the first and second covers 144, 146 over the conductive element 112a,b,d, is formed into a coil shape and then mechanically constrained.

Thereafter, the composite structure undergoes thermal annealing or stress relieving in a chamber, as previously described. The temperature of the chamber is about 130° C. to about 210° C. for about 30 seconds to about 30 minutes to allow the polymeric material to form jacket 130 over conductive element 112a,b,d, after which time the mechanical constraint is removed.

The fifth embodiment listed in Table 1 relates to a jacket 130 formed of a first, second and third covers 144, 146, 148. First cover 144 of ETFE can possess a thickness that ranges from about 0.0005 inches to about 0.0015 inches of extruded ETFE. In another embodiment, first cover 144 can possess a thickness that ranges from about 0.00020 inches to about 0.001 inches. First cover 144 of ETFE is formed by extruding the ETFE over a conductive element 112a,b,d. After the first cover 144 of ETFE has been formed, a second cover 146 of ETFE is introduced over the first cover 144. Second cover 146 can possess a thickness that ranges from about 0.00020 inches to about 0.001 inches. A third cover 148 of FEP is introduced over the second cover 146 in which the third cover 148 can possess a thickness that ranges from about 0.00020 inches to about 0.001 inches. A composite structure is composed of the first, second, and third covers 144, 146, 148 respectively, over the conductive element 112a,b,d. The composite structure is formed into a coil shape and then mechanically constrained, as previously described.

The composite structure then undergoes thermal annealing or stress relieving in a chamber. The temperature in the chamber is about 130° C. to about 210° C. for about 30 seconds to about 30 minutes to allow the polymeric material to form jacket 130 around conductive element 112a,b,d. Thereafter, the mechanical constraint is removed.

The sixth embodiment listed in Table 1 involves a first cover 144 of ETFE followed by a second cover 146 of FEP. First cover 144 of ETFE can possess a thickness that ranges from about 0.0005 inches to about 0.0015 inches of extruded ETFE. In another embodiment, first cover 144 can possess a thickness that ranges from about 0.00020 inches to about 0.001 inches. After the first cover 144 of ETFE has been formed, a second cover 146 of perfluoroalkoxy (PFA) is introduced over the first cover 144. Second cover 146 can possess a thickness that ranges from about 0.00020 inches to about 0.001 inches. In another embodiment, second cover 146 can possess a thickness that ranges from about 0.00020 inches to about 0.003 inches. The composite structure, comprised of the first and second covers 144, 146 over the conductive element 112a,b,d, is formed into a coil shape and then mechanically constrained.

Thereafter, the composite structure undergoes thermal annealing or stress relieving in a chamber, as previously described. The temperature of the chamber is about 130° C. to about 210° C. for about 30 seconds to about 30 minutes to allow the polymeric material to form jacket 130 over conductive element 112a,b,d, after which time the mechanical constraint is removed.

The seventh embodiment listed in Table 1 relates to a jacket 130 formed of a first, second and third covers 144, 146, 148. First cover 144 of ETFE can possess a thickness that ranges from about 0.0005 inches to about 0.0015 inches of extruded ETFE. In another embodiment, first cover 144 can possess a thickness that ranges from about 0.00020 inches to about 0.001 inches. First cover 144 of ETFE is formed by extruding the ETFE over a conductive element 112a,b,d. After the first cover 144 of ETFE has been formed, a second cover 146 of ETFE is introduced over the first cover 144. Second cover 146 can possess a thickness that ranges from about 0.00020 inches to about 0.001 inches. A third cover 148 of PFA is introduced over the second cover 146 in which the third cover 148 can possess a thickness that ranges from about 0.00020 inches to about 0.001 inches. A composite structure is composed of the first, second, and third covers 144, 146, 148 respectively, over the conductive element 112a,b,d. The composite structure is formed into a coil shape and then mechanically constrained, as previously described.

The composite structure then undergoes thermal annealing or stress relieving in a chamber. The temperature in the chamber is about 130° C. to about 210° C. for about 30 seconds to about 30 minutes to allow the polymeric material to form jacket 130 around conductive element 112a,b,d. Thereafter, the mechanical constraint is removed.

The eighth embodiment listed in Table 1 relates to a jacket 130 formed of a first cover 144. First cover 144 of polyflourotetraethylene (PTFE) such as PTFE (extruded and non-porous) can possess a thickness that ranges from about 0.0005 inches to about 0.0015 inches of extruded ETFE. In another embodiment, first cover 144 can possess a thickness that ranges from about 0.00020 inches to about 0.003 inches. A composite structure is composed of the first cover 144 over the conductive element 112a,b,d. The composite structure is formed into a coil shape and then mechanically constrained, as previously described.

The composite structure then undergoes thermal annealing or stress relieving in a chamber. The temperature in the chamber is about 130° C. to about 210° C. for about 30 seconds to about 30 minutes to allow the polymeric material to form jacket 130 around conductive element 112a,b,d. Thereafter, the mechanical constraint is removed.

The ninth embodiment listed in Table 1 relates to a jacket 130 formed of a first, and second covers 144, 146. First cover 144 of PTFE (extruded and nonporous) can possess a thickness that ranges from about 0.0005 inches to about 0.0015 inches of extruded PTFE (extruded and nonporous). Unlike other polymers, PTFE is not melt-processable. Fully dense or non-porous PTFE can be produced via a "paste extrusion" process. With this process a very fine PTFE resin is mixed with a hydrocarbon extrusion aid (e.g. mineral spirits etc.) and compressed to form a billet called a preform, which is "ram extruded" at high pressures. The resulting extruded form is then thermally treated to remove the extrusion aid and sinter the fine particles of PTFE together.

In another embodiment, first cover 144 can possess a thickness that ranges from about 0.00020 inches to about 0.003 inches. In another embodiment, first cover 144 can possess a thickness that ranges from about 0.00020 inches to about 0.001 inches. First cover 144 of PTFE (extruded and nonporous) is formed by extruding the PTFE (extruded and nonporous) over a conductive element 112a,b,d. After the first cover 144 of PTFE (extruded and nonporous) has been formed, a second cover 146 of PTFE (extruded and nonporous) is introduced over the first cover 144. Second cover 146 can possess a thickness that ranges from about 0.00020 inches to about 0.001 inches. A composite structure is composed of the first, and second covers 144, 146 respectively, over the conductive element 112a,b,d. The composite structure is formed into a coil shape and then mechanically constrained, as previously described.

The composite structure then undergoes thermal annealing or stress relieving in a chamber. The temperature in the chamber is about 130° C. to about 210° C. for about 30 seconds to about 30 minutes to allow the polymeric material to form jacket 130 around conductive element 112a,b,d. Thereafter, the mechanical constraint is removed.

The tenth embodiment listed in Table 1 relates to a jacket 130 formed of a first, second and third covers 144, 146, 148. First cover 144 of PTFE (extruded and nonporous) can possess a thickness that ranges from about 0.0005 inches to about 0.0015 inches of PTFE (extruded and nonporous). In another embodiment, first cover 144 can possess a thickness that ranges from about 0.00020 inches to about 0.001 inches. First cover 144 of PTFE (extruded and nonporous) is formed by extruding the PTFE (extruded and nonporous) over a conductive element 112a,b,d. After the first cover 144 of PTFE (extruded and nonporous) has been formed, a second cover 146 of PTFE (extruded and nonporous) is introduced over the first cover 144. Second cover 146 can possess a thickness that ranges from about 0.00020 inches to about 0.001 inches. A third cover 148 of fluorinated ethylene propylene (FEP) is introduced over the second cover 146 in which the third cover 148 can possess a thickness that ranges from about 0.00020 inches to about 0.001 inches. A composite structure is composed of the first, second, and third covers 144, 146, 148 respectively, over the conductive element 112a,b,d. The composite structure is formed into a coil shape and then mechanically constrained, as previously described.

The composite structure then undergoes thermal annealing or stress relieving in a chamber. The temperature in the chamber is about 130° C. to about 210° C. for about 30 seconds to about 30 minutes to allow the polymeric material to form jacket 130 around conductive element 112a,b,d. Thereafter, the mechanical constraint is removed.

The eleventh embodiment listed in Table 1 relates to a jacket 130 formed of a first, second and third covers 144, 146, 148. First cover 144 of PTFE (extruded and nonporous) can possess a thickness that ranges from about 0.0005 inches to about 0.0015 inches of PTFE (extruded and nonporous). In another embodiment, first cover 144 can possess a thickness that ranges from about 0.00020 inches to about 0.001 inches. First cover 144 of PTFE (extruded and nonporous) is formed by extruding the PTFE (extruded and nonporous) over a conductive element 112a,b,d. After the first cover 144 of PTFE (extruded and nonporous) has been formed, a second cover 146 of PTFE (extruded and nonporous) is introduced over the first cover 144. Second cover 146 can possess a thickness that ranges from about 0.00020 inches to about 0.001 inches. A third cover 148 of PFA is introduced over the second cover 146 in which the third cover 148 can possess a thickness that ranges from about 0.00020 inches to about 0.001 inches. A composite structure is composed of the first, second, and third covers 144, 146, 148 respectively, over the conductive element 112a,b,d. The composite structure is formed into a coil shape and then mechanically constrained, as previously described.

The composite structure then undergoes thermal annealing or stress relieving in a chamber. The temperature in the chamber is about 130° C. to about 210° C. for about 30 seconds to about 30 minutes to allow the polymeric material to form jacket 130 around conductive element 112a,b,d. Thereafter, the mechanical constraint is removed.

The tenth embodiment listed in Table 1 relates to a jacket 130 formed of a first, second and third covers 144, 146, 148. First cover 144 of PTFE (extruded and nonporous) can possess a thickness that ranges from about 0.0005 inches to about 0.0015 inches of PTFE (extruded and nonporous). In another embodiment, first cover 144 can possess a thickness that ranges from about 0.00020 inches to about 0.001 inches. First cover 144 of PTFE (extruded and nonporous) is formed by extruding the PTFE (extruded and nonporous) over a conductive element 112a,b,d. After the first cover 144 of PTFE (extruded and nonporous) has been formed, a second cover 146 of PTFE (extruded and nonporous) is introduced over the first cover 144. Second cover 146 can possess a thickness that ranges from about 0.00020 inches to about 0.001 inches. A third cover 148 of ethylene-tetraflouroethylene based copolymer (EFEP) is introduced over the second cover 146 in which the third cover 148 can possess a thickness that ranges from about 0.00020 inches to about 0.001 inches. A composite structure is composed of the first, second, and third covers 144, 146, 148 respectively, over the conductive element 112a, b,d. The composite structure is formed into a coil shape and then mechanically constrained, as previously described.

The composite structure then undergoes thermal annealing or stress relieving in a chamber. The temperature in the chamber is about 130° C. to about 210° C. for about 30 seconds to about 30 minutes to allow the polymeric material to form jacket 130 around conductive element 112a,b,d. Thereafter, the mechanical constraint is removed.

Table 1, presented below, summarizes the various embodiments of jacket 130.

TABLE 1

Embodiments of jacket 130 that comprise one or more polymeric compounds

| No. | First Cover | Second Cover | Third Cover | N Cover |
|---|---|---|---|---|
| 1 | ETFE | | | |
| 2 | ETFE | ETFE | | |
| 3 | ETFE | ETFE | ETFE | |
| 4 | ETFE | FEP | | |
| 5 | ETFE | ETFE | FEP | |
| 6 | ETFE | PFA | | |
| 7 | ETFE | ETFE | PFA | |
| 8 | PTFE (extruded, nonporous) | | | |
| 9 | PTFE (extruded, nonporous) | PTFE (extruded, nonporous) | | |
| 10 | PTFE (extruded, nonporous) | PTFE (extruded, nonporous) | FEP | |
| 11 | PTFE (extruded, nonporous) | PTFE (extruded, nonporous) | PFA | |
| 12 | PTFE (extruded, nonporous) | PTFE (extruded, nonporous) | EFEP | |

The insulated conductive element formed through jacket 130 over conductive element 112a,b,d can be helically wrapped around a mandrel (not shown). After winding the insulated cable onto the mandrel and mechanically restraining this composite structure, the polymeric material over the conductive element (e.g. cable etc.) can be annealed to minimize springback and allow the conductive element (e.g. cable etc.) to retain its coiled shape. After being removed from the mandrel, the conductive element (e.g. cable etc.) retains its coiled shape.

Figure 5A:
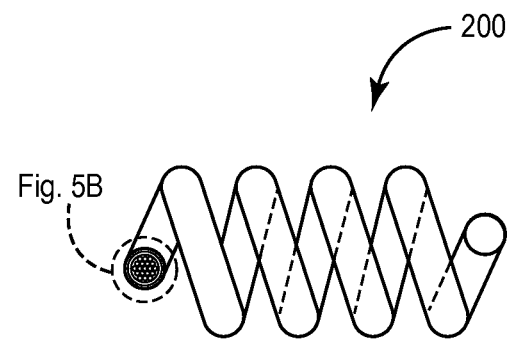
FIG. 5A is a schematic view of an exemplary insulated conductive element.
Figure 5B:
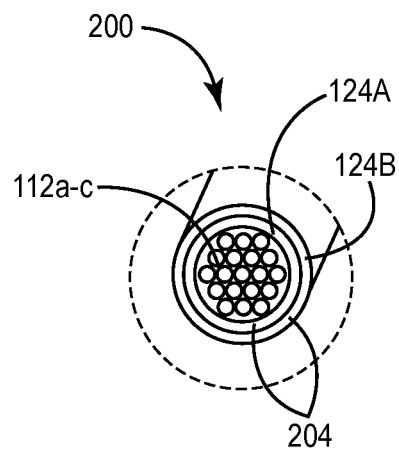
FIG. 5B is a cross-sectional view of the insulated conductive element depicted in FIG. 5A.

Insulated conductive element 200 is depicted in FIGS. 5A-5B. Insulated conductive element 200 includes a conductive element 112a,b,d (i.e. cable, coiled cable etc.) with a thin polymeric material 204 or cover that has been thermally processed (e.g. annealed etc.) to conductive element 112a,b, d. Polymeric material 204 comprises a first and second covers 124a, 124b. Conductive element 112a,b,d has an outer diameter of about 0.09 inches or less. In one embodiment, conductive element 112a,b,d can be a 1×19 cable construction with filaments composed of MP35N/Ag core.

Figure 6A:
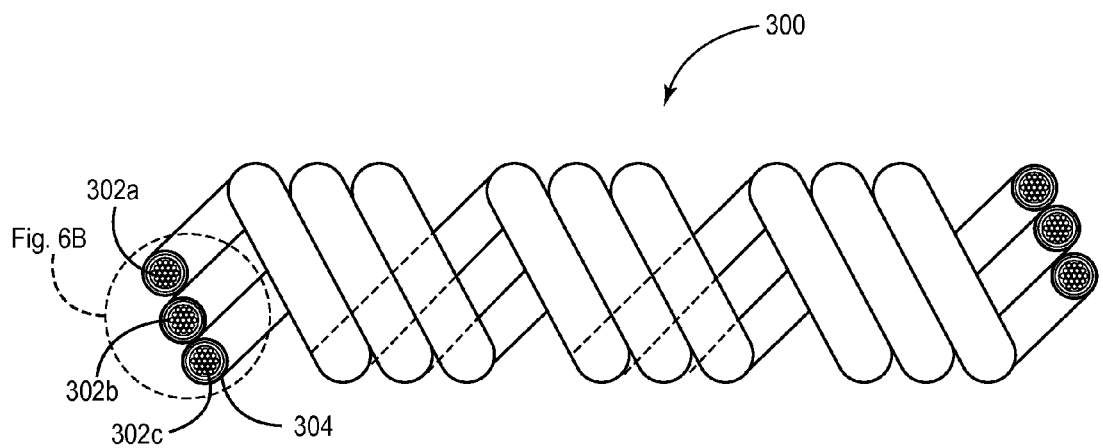
FIG. 6A is a schematic view of an exemplary insulated multi-conductor element.
Figure 6B:
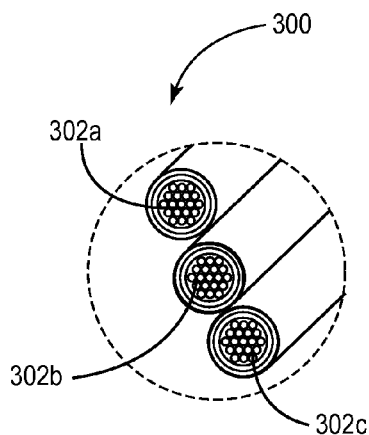
FIG. 6B is a schematic cross-sectional view of an exemplary insulated multi-conductor element depicted in FIG. 6A.

Referring to FIGS. 6A-6B, an insulated conductive element 300 is depicted that comprises a set of conductors 302a-c (i.e. three conductors) and an insulative layer or cover 304. Conductive element 300 such as a 1×19 cable MP35N/Ag core and has an outer diameter of about 0.055 inches. Insulative layer 304 comprises a layer of PEEK and a layer of ETFE. In one embodiment, each layer of PEEK and ETFE is about 0.0008 inches or less. In another embodiment, each layer of PEEK and ETFE is about 0.002 inches or less.

Figure 7A:
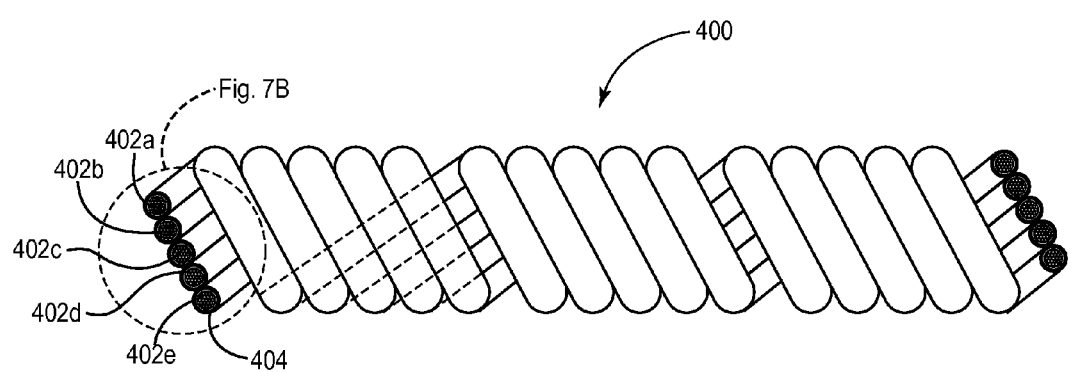
FIG. 7A is a schematic view of another exemplary insulated multi-conductor element.
Figure 7B:
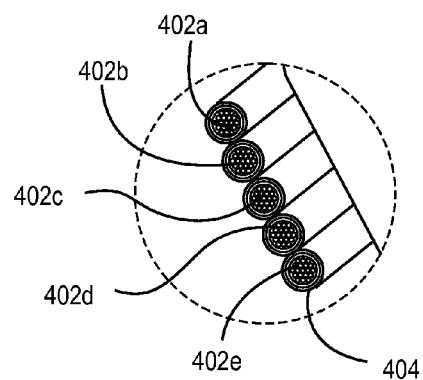
FIG. 7B is a schematic cross-sectional view of an exemplary insulated multi-conductor element depicted in FIG. 7A.

Referring to FIG. 7A-7B, insulated conductive element 400 comprises a set of conductors 402a-e (i.e. five conductors) and an insulative layer or cover 404. Conductive element 400 has an outer diameter of about 0.060 inches and is a 1×19 cable. Insulative layer 404 comprises a layer of PEEK and a layer of ETFE. In one embodiment, each layer of PEEK and ETFE is about 0.0008 inches or less. In another embodiment, each layer of PEEK and ETFE is about 0.002 inches or less.

Figure 8A:
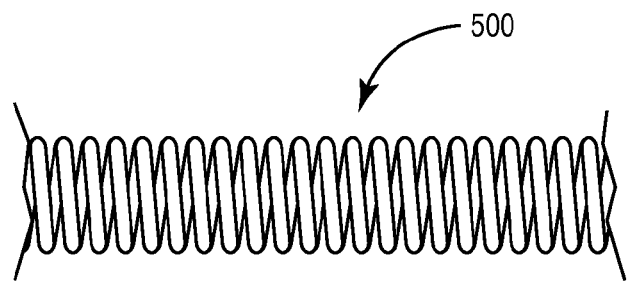
FIG. 8A is a schematic view of an exemplary insulated multi-conductor element before its stretched.
Figure 8B:
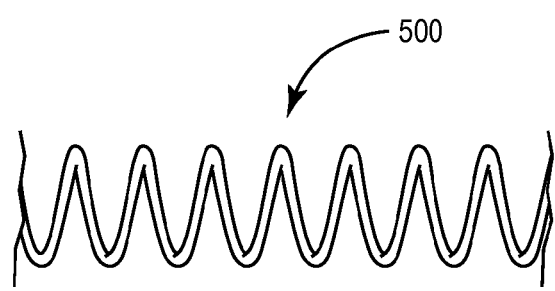
FIG. 8B is a schematic view of an exemplary insulated multi-conductor element being stretched.
Figure 8C:
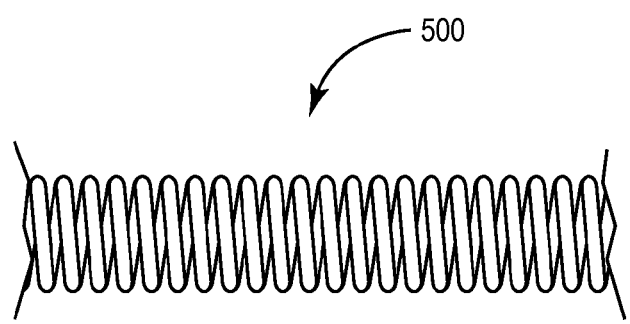
FIG. 8C is an exemplary insulated multi-conductor element in a relaxed position and returning to its original coiled shape.

Referring to FIGS. 8A-8C, jacketed conductive element 500 is shown as retaining its coiled shape despite being stretched. Conductive element 500 comprises a 1×19 cable construction with filaments composed of MP35N/Ag core with an insulative or jacketed layer, coating or cover. The insulative layer comprises a layer of PEEK and a layer of ETFE. In one embodiment, each layer of PEEK and ETFE is about 0.0008 inches or less. In one embodiment, each layer of PEEK and ETFE is about 0.002 inches or less. Referring to FIG. 8A, insulated conductive element 500 is depicted in a relaxed position (FIG. 8A) over a mandrel. While over the mandrel, conductive element 500 is thermally annealed. Referring to FIG. 8B, insulated conductive element 500 is depicted in a stretched position. Thereafter, insulated conductive element 500 moves to a relaxed position after being stretched (FIG. 8C). The insulated conductive element 500 retains 99% or more of its original coiled shape. In another embodiment, insulated conductive element 500 comprises 95% or more of its original coiled shape.

Figure 9:
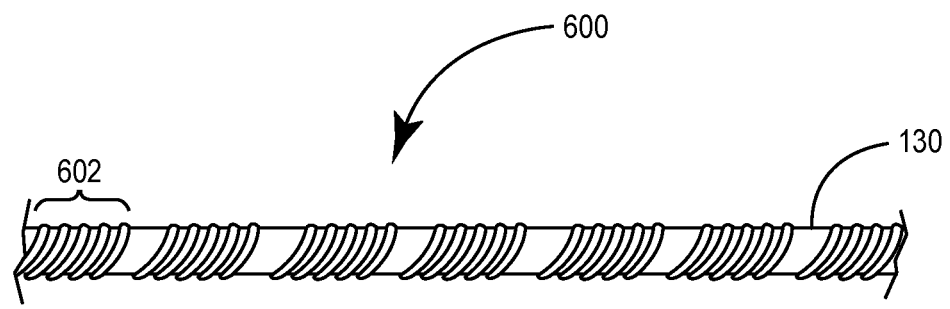
FIG. 9 is a schematic view of an exemplary insulated multi-conductor element wrapped around a tubular insulative element or a coil liner.
Figure 10A:
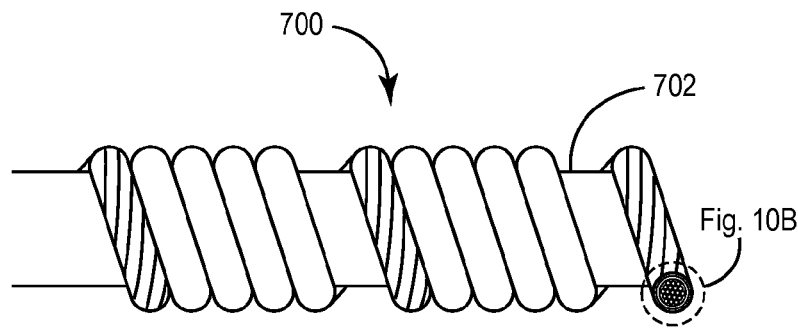
FIG. 10A is a schematic view of yet another exemplary insulated multi-conductor element wrapped around a mandrel.
Figure 10B:
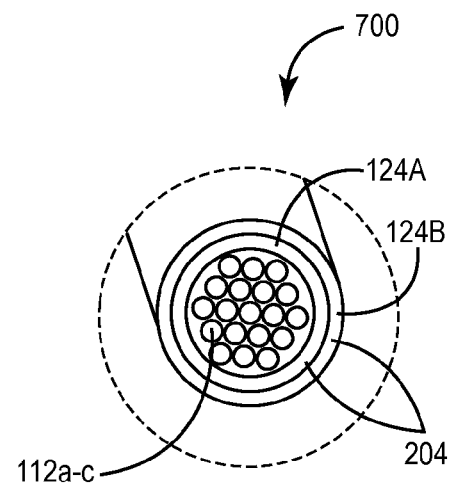
FIG. 10B is a cross-sectional view of the insulated conductive element depicted in FIG. 10A.

Referring to FIG. 9, insulated conductive element 600 is helically wrapped around a coil liner 130. Insulated conductive element 600 comprises a set of jacketed conductors 602 (i.e. five conductors cable-coil). Referring to FIG. 10A-10B, insulated conductive element 700 is helically wrapped around a mandrel 702. Insulated conductive element 700 comprises a set of conductors 702 (i.e. five conductors) and an insulative layer or cover.

Figure 11:
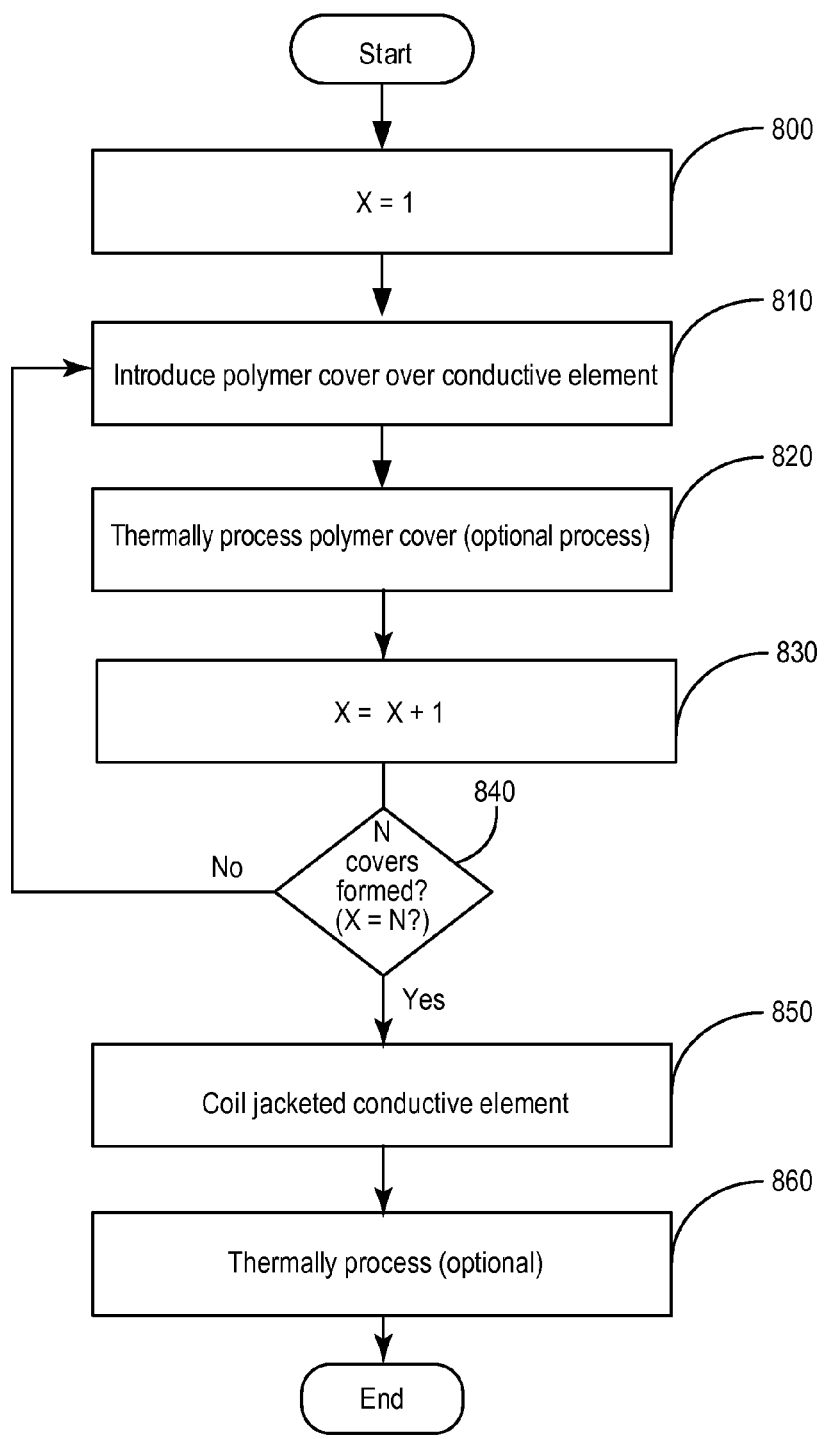
FIG. 11 is a flow diagram for forming a coiled jacketed conductive element.

FIG. 11 is a flow diagram of an exemplary computer-implemented method or a manual process to form at least one cover of PEEK over the conductive element. At block 800, a counter, x, is initiated to 1 in order to count the number polymer covers formed over a conductive element. At block 810, a polymer is extruded (also referred to as introduced) over the conductive element. Polymers with high elastic modulus (i.e. stiffness) such as PEEK are preferred since PEEK can be annealed or stress relieved to increase crystallinity and set the coil shape in conductive element 112a-c. At block 820, the polymer cover can undergo an optional thermal process.

At block 830, the counter, X, is incremented by adding 1 to the previous value of X. At block 840, a determination is made as to whether a sufficient number of polymer covers have been formed over the conductive element. In this embodiment, a determination is made as to whether X=N where N equals the number of pre-selected covers to be added to the conductive element. If X does not equal N, the process control returns to block 810 to extrude the same or different polymer over the previous polymer cover. If x does equal N, then the process goes to block 850, where the jacketed conductive element undergoes coiling, as previously described. If x does not equal N, the process returns to introducing another polymeric cover over the conductive element 112a-d. If x does equal N, no additional polymer covers are introduced over the conductive element 112a-d. At block 850, the jacketed conductive element is formed into a coil. At block 860, the coiled jacketed conductive element can undergo an optional thermal process. If the method is implemented on a computer, the number of polymeric covers formed over the conductive element and/or the types of polymeric material used for each cover can be displayed on a graphical user interface of a computer. The computer-implemented instructions are executed on a processor of a computer.

Co-pending U.S. patent application Ser. No. 12/211,093 entitled "MEDICAL ELECTRICAL LEAD" filed by Gregory A. Boser and Kevin R. Seifert and assigned to the same Assignee as the present invention. This co-pending application is hereby incorporated herein by reference in its entirety.

Co-pending U.S. patent application Ser. No. 12/211,065 entitled "MEDICAL ELECTRICAL LEAD" filed by Gregory A. Boser and Kevin R. Seifert and assigned to the same Assignee as the present invention. This co-pending application is hereby incorporated herein by reference in its entirety.

Co-pending U.S. patent application Ser. No. 12/211,092 entitled "MEDICAL ELECTRICAL LEAD" filed by Gregory A. Boser and Kevin R. Seifert and assigned to the same Assignee as the present invention. This co-pending application is hereby incorporated herein by reference in its entirety.

The description of the invention is merely exemplary in nature and, thus, variations that do not depart from the gist of the invention are intended to be within the scope of the invention. Such variations are not to be regarded as a departure from the spirit and scope of the invention.

The invention claimed is:

1. A medical electrical lead, comprising:
A lead body that comprises a conductive element; wherein the conductive element is covered by a jacket and wherein the jacket comprises first and second covers, the first cover being of extruded polytetrafluoroethylene (PTFE) directly contacting the conductive element and the second cover comprising one of PTFE, ethylene-tetrafluoroethylene (ETFE), ethylene-tetrafluorosthylene based copolymer (EFEP), perfluoroalkoxy (PFA) and fluorinated ethylene propylene (FEP, and
wherein the conductive element is a coiled, cabled conductor that after coiling has a diameter of up to 95% of a coiled diameter of the conductive element otherwise resulting from springback after coiling in the absence of the jacket.

2. The medical electrical lead of claim 1 further comprising a third cover comprising one of PTFE, ETFE, and EFEP.

3. The medical electrical lead of claim 1 further comprising:
a third cover of a polymeric material coupled to the first cover, wherein the third cover comprises one of ETFE, PEP, PFA and EFEP.

4. A medical electrical lead, comprising:
A lead body that comprises a conductive element; wherein the conductive element comprises a multiple filar cabled conductor and is covered by a jacket and wherein the jacket comprises first and second covers, the first cover being of extruded polytetrafluoroethylene (PTFE) directly contacting the conductive element and the second cover comprising one of PTFE, ethylene-tetrafluoroethylene (ETFE), ethylene-tetrafluorosthylene based copolymer (EFEP), perfluoroalkoxy (PFA) and fluorinated ethylene propylene (FEP, and
wherein the conductive element is a coiled, cabled conductor that after coiling has a diameter of up to 95% of a coiled diameter of the conductive element otherwise resulting from springback after coiling in the absence of the jacket.

5. The medical electrical lead of claim 1 further comprising a third cover comprising one of PTFE, ETFE, and EFEP.

6. The medical electrical lead of claim 1 further comprising:
a third cover of a polymeric material coupled to the first cover, wherein the third cover comprises one of ETFE, PEP, PFA and EFEP.

* * * * *